United States Patent
Li et al.

(10) Patent No.: US 9,572,857 B2
(45) Date of Patent: Feb. 21, 2017

(54) PHARMACEUTICAL COMPOSITIONS WITH ENHANCED STABILITY

(71) Applicants: Yuhua Li, Landenberg, PA (US); Benjamin Chien, Woodside, CA (US)

(72) Inventors: Yuhua Li, Landenberg, PA (US); Benjamin Chien, Woodside, CA (US)

(73) Assignee: Foresee Pharmaceuticals Co., Ltd., Taipei (TW)

( * ) Notice: Subject to any disclaimer, the term of this patent is extended or adjusted under 35 U.S.C. 154(b) by 0 days.

(21) Appl. No.: 15/230,413

(22) Filed: Aug. 6, 2016

(65) Prior Publication Data

US 2016/0331802 A1    Nov. 17, 2016

Related U.S. Application Data

(63) Continuation of application No. 11/653,636, filed on Jan. 16, 2007.

(60) Provisional application No. 60/759,891, filed on Jan. 18, 2006.

(51) Int. Cl.
  *A61K 38/09*  (2006.01)
  *A61K 9/00*  (2006.01)
  *A61K 47/34*  (2006.01)
  *A61K 47/22*  (2006.01)

(52) U.S. Cl.
  CPC ............ *A61K 38/09* (2013.01); *A61K 9/0024* (2013.01); *A61K 47/22* (2013.01); *A61K 47/34* (2013.01)

(58) Field of Classification Search
  None
  See application file for complete search history.

(56) References Cited

U.S. PATENT DOCUMENTS

| 6,565,874 B1 | 5/2003 | Dunn et al. |
| 6,630,155 B1 | 10/2003 | Chandrashekar et al. |
| 6,773,714 B2 * | 8/2004 | Dunn ............... A61K 9/0024 424/422 |
| 2005/0042294 A1 * | 2/2005 | Thanoo ............ A61K 9/0019 424/486 |

OTHER PUBLICATIONS

Bastin et al. in Organic Process Research & Development 2000, 4, 427-435.*

* cited by examiner

*Primary Examiner* — Dennis Heyer
(74) *Attorney, Agent, or Firm* — VLP Law Group LLP; Kent H. Cheng (57) ABSTRACT

The present invention provides for a stabilized biodegradable polymeric composition useful as a controlled release delivery system for peptide agents. The compositions of the present invention comprise a) a beneficial salt of a peptide agent formed with a strong acid that minimizes or prevents the interaction/reaction between the peptide agent and the polymer in an organic solution; b) a biodegradable polymer; c) a pharmaceutically acceptable organic solvent; and d) optionally one or more excipients. The present invention also relates to a method of manufacturing and a method of use thereof.

7 Claims, 3 Drawing Sheets

Figure 1. Stability of LA in Formulations at 4 °C after 16 Months

Figure 2. Molecular Weight of PLGA in Formulations at 4 °C after 16 Months

Figure 3: Effect of type and concentration of PLGA on the release of leuprolide

Figure 4. Effect of vitamin E on the release of LA from injectable compositions

Figure 5. Effect of Miglyol 812 on the release of LA from injectable compositions Figure 6. Release profile of LA from injectable polymeric compositions following SC administration in rats

PHARMACEUTICAL COMPOSITIONS WITH ENHANCED STABILITY

BACKGROUND OF THE INVENTION

In recent years, a large number and variety of peptide agents such as peptides, oligopeptides, polypeptides, and proteins have been discovered and have received much attention as drug candidates. However, many peptide agents are not stable as they are easily hydrolyzed or degraded in vivo by enzymes resulting in a very short circulation half-life. Therefore, most of peptide medicines have been administered by injection, typically multiple times per day.

Injection administration, however, is painful, very costly, and inconvenient. Often, the patient compliance is very challenging. For many peptide agents, particularly hormones, it requires the drug to be delivered continuously at a controlled rate over a long period of time, and thus a controlled release delivery system is desirable. Such systems may be provided by incorporating the peptide agents in biodegradable and biocompatible polymer matrices. In one approach the polymer is dissolved in an organic solvent and then mixed with the peptide agents that is fabricated into the forms of microcapsules, microgranules or implantable rods by removing the organic solvent. The peptide agent is entrapped within the polymer matrices. Several products have been successfully developed by using biodegradable polymers in the forms of microparticles and solid rod implants, such as Lupron, Zoladex, Triptorelin, etc. Although these products appear to be effective, but they have drawbacks and limitations, such as the large volume of suspending fluids for microparticles or surgical insertion of solid implants. These products are not very patient friendly. In addition, the manufacturing processes for producing sterile and reproducible products are complicated, resulting in high cost of manufacturing. It is highly desirable that a composition can be manufactured and used easily.

In another approach, the biodegradable polymer and the peptide agents are dissolved in a biocompatible organic solvent to provide a liquid composition. When the liquid composition is injected into the body, the solvent dissipates into the surrounding aqueous environment, and the polymer forms a solid or gel depot from which the bioactive agent is released over a long period of time. The following references U.S. Pat. Nos. 6,565,874; 6,528,080; RE37, 950; 6,461,631; 6,395,293; 6,355,657; 6,261,583; 6,143,314; 5,990,194; 5,945,115; 5,792,469; 5,780,044; 5,759,563; 5,744,153; 5,739,176; 5,736,152; 5,733,950; 5,702,716; 5,681,873; 5,599,552; 5,487,897; 5,340,849; 5,324,519; 5,278,202; 5,278,201; and 4,938,763 are believed to be representative in this area and are incorporated herein by reference. Notwithstanding some success, those methods have not been entirely satisfactory for a large number of peptide agents that may be effectively delivered by such an approach.

It is well recognized in the art that bioactive agent containing basic functional groups interacts with biodegradable polymer to catalyze (or expedite) the degradation of the polymer and form conjugate with the polymer and/or its degradation products. The interaction/reaction between the basic bioactive agents and polymer carriers may occur: 1) during formulation when the basic bioactive agents are incorporated in the polymer carrier, such as microencapsulation, injection molding, extrusion molding, mixing with polymer solutions in organic solvent, and the like; 2) during storage and 3) during the process of biodegradation and the release of bioactive agents in vivo.

It is known that the degradation of peptide agents and biodegradable polymers, and reactions between the two typically occur much faster in solution than in a dry, solid state. The interaction/reaction between bioactive agents containing basic functional groups, i.e., amines, and polymers during the microparticle formation process using solvent evaporation/extraction methods where the bioactive agent and polymer were dissolved/dispersed in non-polar organic solvents were disclosed [Krishnan M. and Flanagan D R., *J Control Release*. 2000 Nov. 3; 69(2): 273-81]. Significant amount of amide moieties were formed. It was clearly shown that commonly used solvents for fabrication of biodegradable polymer drug delivery systems could permit rapid reaction between bioactive agent and polymer. In another disclosure, the accelerated degradation of polymers by organic amines in polar protic organic solvent (e.g., methanol) was also reported [Lin W J, Flanagan D R, Linhardt R J. *Pharm Res*. 1994 July; 11(7):1030-4].

Since the controlled release delivery system is commonly fabricated through a step that involves dissolving/dispersing peptide agent into biodegradable polymer solution in an organic solvent, the stabilization of all the components in the composition at this step represents a very significant formulation challenge. One common approach that has been used to overcome the challenge of manufacturing and storage stability of peptide agent and biodegradable polymer in solution or suspension is to keep the peptide agent and the polymer solution in two separate containers and mix them just before use. This assumes that the organic solvent may be separated from polymeric matrix quickly through diffusion, extraction or evaporation after the peptide agents and polymer solution are mixed. An example was disclosed in U.S. Pat. Nos. 6,565,874 and 6,773,714 that describe polymeric delivery formulations of leuprolide acetate that is related to a commercial product Eligard® for treatment of prostate cancer. In order to maintain the stability of the formulations, this product is supplied in separate syringes and the contents in the syringes are mixed just before use. However, because of the viscous nature of the polymer formulations, it is often difficult to mix the contents in two separated syringes by end users. The uniformity of the formulations prepared by the end-user may vary significantly where contamination may also occur and the quality of the treatment can be compromised significantly. In addition, this approach will not prevent the interaction between the peptide agent and polymer during mixing and administration. As disclosed in US20060034923 A1, when octreotide acetate was combined with polylactide-co-glicolide solution in NMP, more than 40% of octreotide was acylated within 5 hours. This modification of the peptide may lead to a significant loss of activity or change of immunogenicity. The molecular weight of the polymer also decreased significantly within the same time period. This fast degradation of the peptide and polymer will alter the release profile of the peptide and result in a compromised treatment outcome. Therefore, precise control for the preparation process and time is critical and this significantly increases the difficulty for end-user. Furthermore, the in vivo formation of the implant from the injectable polymeric composition is not instantaneous. Typically the solvent dissipation process can take a few hours to several days depending upon the solvents used. During this period, the presence of an organic solvent could also promote the interaction/reaction between the peptide agents and the polymer. Therefore, there is a need to develop a pharmaceutical composition that will minimize or prevent the interaction/reaction between the peptide agent and the polymer in an organic solution. There is a further need to develop a pharmaceutical composition that is stable with a satisfactory storage shelf life in a ready-to-use product configuration.

SUMMARY OF THE INVENTION

It was surprisingly discovered that injectable biodegradable polymeric compositions comprising peptide agents in the form of a salt formed with a strong acid (e.g., hydrochloric acid) exhibit much higher stability than those in the form of a salt formed with a weak acid (e.g., acetic acid) or in the form of the free base. Such beneficial salts of peptide agents may be formed through the neutralization of any basic groups of the peptide agents with a strong acid. When such beneficial salts of peptide agents formed with a strong acid were formulated into injectable biodegradable polymeric compositions, the interactions/reactions between the peptide agents and the polymer are minimized or prevented. Using such beneficial salts of peptide agents formed with a strong acid allows for the preparation of a stabilized injectable composition pre-filled in a single syringe in a ready-to-use configuration with satisfactory storage stability. The use of the salt of peptide agent formed with a strong acid of the present invention to enhance the stability of the injectable polymeric compositions is not contemplated by the prior art.

Accordingly, the present invention provides a stabilized injectable biodegradable polymeric composition for forming an economical, practical, and efficient controlled release delivery system for peptide agents. The present invention also provides a method of manufacturing and a method of use thereof. According to the present invention, the drug delivery system is produced easily and delivered conveniently to a subject such as a mammal or human. The compositions deliver therapeutic amount of peptide agents over a desired, extended period of time, preferably from several weeks to one year. The compositions are both biocompatible and biodegradable, and disappear harmlessly after delivering the dose of the peptide agents.

The compositions in accordance with the present invention comprise a) a beneficial salt of a peptide agent formed with a strong acid that minimizes or prevents the interaction/reaction between the peptide agent and the polymer in an organic solution; b) a biodegradable polymer; c) a pharmaceutically acceptable organic solvent. According to the invention, the pharmaceutical composition may optionally include excipients to achieve optimal delivery of the peptide agent. The pharmaceutical composition may be a viscous or non-viscous liquid, gel or semisolid that moves as a fluid so that it may be injected using a syringe. The pharmaceutical composition may be pre-filled into one syringe to form a product in a ready-to-use configuration.

The peptide agent of the present invention contains at least one basic group. The peptide agent may be any peptide, oligopeptide, polypeptide, or protein that is capable of providing a biological, physiological or therapeutic effect in an animal or human. The peptide agent may be any one or more of known biologically active peptide, oligopeptide, polypeptide, or protein recognized in any documents cited herein or otherwise recognized in the art. The peptide agent may also stimulate or inhibit a desired biological or physiological activity within the animal or human, including without limitation, stimulate an immunogenic or immunological response.

According to one embodiment of the present invention, the peptide agent has an N-terminus that is not a primary amine (e.g., LHRH agonists, such as leuprorelin, goserelin, LHRH antagonists, such as cetrorelix, enfuvirtide, thymosin abarelix, and the like). In another embodiment of the present invention, the peptide agent has either an N-terminal primary amine or side chain primary amine group covalently modified with hydrophilic and/or lipophilic moieties that may be produced through pegylation, acylation, and the like. Furthermore, both N-terminal primary amine and side chain primary amine groups of the peptide agent may also be covalently modified simultaneously with hydrophilic and/or lipophilic moieties through pegylation, acylation, and the like.

The strong acid may be any acid having a pKa in water less than 3, preferably less than 0, more preferably less than −3. For example, a strong acid may be selected from, but not limited to, the group consisting of hydrochloric acid, hydrobromic acid, sulfuric acid, organic sulfuric acids, alkyl sulfuric acids of 1-40 carbons, nitric acid, chromic acid, methanesulfonic acid, trifluromethane sulfonic acid, organic sulfonic acids, trichloroacetic acid, dichloroacetic acid, bromoacetic acid, chloroacetic acid, cyanoacetic acid, 2-chloropropanoic acid, 2-oxobutanoic acid, 2-chlorobutanoic acid, 4-cyanobutanoic acid, perchloric acid, phosphoric acid, hydrogen iodide, and the like.

The biodegradable polymer can be any biocompatible and pharmaceutically acceptable polymers. The biodegradable polymers may be thermoplastic, which melts upon heating and solidifies upon cooling. The biodegradable polymers of the invention are substantially insoluble in aqueous or body fluid, but are capable of substantially dissolving or dispersing in a water-miscible organic solvent to form a solution or suspension. Upon contact with an aqueous fluid, the water-miscible organic solvent diffuses/dissipates from the inventive composition, which causes the coagulation of the polymer to form a gel, or solid matrix encapsulating the peptide agent. Examples of the polymers suitable for the present composition includes, without limitation, polylactides, polyglycolides, polycaprolactones, polyanhydrides, polyurethanes, polyesteram ides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(maleic anhydride), and copolymers, terpolymers, or combinations or mixtures therein. Lactic acid-based polymers, and copolymers of lactic acid and glycolic acid (PLGA), including poly(D,L-lactide-co-glycolide) and poly(L-lactide-co-glycolide) are preferably used in the present invention. In some embodiments, the PLGA polymers have a weight average molecular weights of between about 2,000 to about 100,000 and monomer ratios of lactic acid to glycolic acid of between about 50:50 to about 100:0.

The pharmaceutically acceptable organic solvents may be selected from a group consisting of N-methyl-2-pyrrolidone, methoxypolyethylene glycol, alkoxypolyethylene glycol, polyethylene glycol esters, glycofurol, glycerol formal, methyl acetate, ethyl acetate, methyl ethyl ketone, dimethylformamide, dimethyl sulfoxide, tetrahydrofuran, caprolactam, decylmethylsulfoxide, benzyl benzoate, ethyl benzoate, triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, ethyl lactate, propylene carbonate, ethylene carbonate, butyrolactone, and 1-dodecylazacyclo-heptan-2-one, and combinations thereof.

According to the present invention, one or more excipients may be incorporated in the inventive composition to achieve optimal delivery of the peptide agent. Suitable excipients may include release rate modifying agents, burst effect reducing materials, buffering materials, antioxidants, and the like.

According to the present invention, suitable release rate modifying agents include, but are not limited to, amphiphilic compounds or copolymers, such alkanecarboxylic acid, oleic acid, alkyl alcohol, polar lipids, surfactants, copolymers of polyethyleneglycol and polylactide or poly(lactide-co-glycolide), poloxamers, polyvinylpyrrolidone, polysorbates, and the like; esters of mono-, di-, and tricarboxylic acids, such as 2-ethoxyethyl acetate, triethyl citrate, acetyl tributyl citrate, acetyl triethyl citrate, glycerol triacetate, di(n-butyl) sebecate, and the like; polyhydroxy alcohols, such as polyethylene glycol, sorbitol, and the like; fatty acids; triesters of glycerol, such as triglycerides, medium-chain triglycerides such as MIGLYOL 810, 812, 818, 829, 840, and the like. Mixtures of rate modifying agents can also be used in the polymer systems of the invention.

According to the present invention, suitable buffering agents include, but are not limited to, inorganic and organic salts including calcium carbonate, calcium hydroxide, calcium myristate; calcium oleate, calcium palmitate, calcium stearate, calcium phosphate, magnesium carbonate, magnesium hydroxide, magnesium phosphate, magnesium myristate, magnesium oleate, magnesium palmitate, magnesium stearate, zinc carbonate, zinc hydroxide, zinc myristate, zinc oleate, zinc palmitate, zinc stearate, zinc phosphate, and combinations thereof.

According to the present invention, suitable antioxidants include, but are not limited to, d-alpha tocopherol acetate, ascorbyl palmitate, butylated hydroxyanidole, butylated hydroxyanisole, butylatedhydroxyquinone, hydroxycomarin, butylated hydroxytoluene, ethyl gallate, propyl gallate, octyl gallate, lauryl gallate, propylhydroxybenzoate, trihydroxybutylrophenone, vitamin E, pegylated vitamin E or vitamin E-TPGS, and the like.

The present invention further provides methods of making and using such compositions. For example, a method of making such compositions comprising the neutralization of basic amine groups of peptide agents to form a beneficial salt to minimize or prevent the interaction/reaction of the basic amine group with the polymer; and the combination of the beneficial salt with other components and optionally one or more excipients. Preferably, the beneficial salt of the peptide agent is formed first, and then combined with the polymer dissolved in an organic solvent. Such compositions are physico-chemically stable prior to and during the fabrication process of a controlled delivery system such as microparticle formation or other implantable matrix formation. Preferably, such injectable compositions are physico-chemically stable during preparation, storage, and subsequent administration to a subject and form consistent and controlled release implants upon administration to a tissue site.

The present invention further provides a kit for administration of the injectable composition to form a consistent and controlled release depot system, the kit comprises: a biodegradable polymer dissolved in a pharmaceutically acceptable solvent; a beneficial salt of a peptide agent containing at least one basic amine group formed with a strong acid dissolved or dispersed in the polymeric vehicle; and optionally one or more excipients. The uniform mixture of all the components is packaged into one container. Preferably, the container is a syringe. Accordingly, the present invention also provides a method comprising a step of filling a syringe with the composition to form a stable product in a ready-to-use configuration.

The present invention further provides a method for in-situ forming implant capable of functioning as a controlled release delivery system of the peptide agent in a subject. The peptide agent is preferably incorporated into the in situ formed implant, and subsequently released into the surrounding tissue fluids and to the pertinent body tissue or organ as the polymer degrades. The method comprises: administration of the injectable compositions of the present invention to an implant site by any suitable method for applying a liquid, as for example, by means of a syringe, needle, cannula, catheter, pressure applicator, and the like.

DETAILED DESCRIPTION OF THE INVENTION

The present invention provides a stabilized injectable biodegradable polymeric composition for forming an economical, practical, and efficient controlled release delivery system for peptide agents. The present invention also provides a method of manufacturing and a method of use thereof.

The compositions of the present invention comprise a) a beneficial salt of a peptide agent formed with a strong acid that minimizes or prevents the interaction/reaction between the peptide agent and the polymer in an organic solution; b) a biodegradable polymer; c) a pharmaceutically acceptable organic solvent. According to the invention, the pharmaceutical composition may optionally include one or more excipients to achieve optimal delivery of the peptide agent. The injectable polymeric composition of the present invention may be a viscous or non-viscous liquid, gel or semisolid that moves as a fluid so that it may be injected using a syringe. The injectable polymeric composition may be pre-filled into one syringe to form a product kit in a ready-to-use configuration.

The controlled release delivery system of the present invention may be formed as an implantable polymeric matrix in vitro, or alternatively, it may be formed in-situ in the forms of a gel or a solid implant. When administered to a subject, the controlled release of the peptide agent can be sustained for a desired period of time depending upon the composition of the implant. With the selections of the biodegradable polymer and other components, the duration of the sustained release of the peptide agent can be controlled over a period of time from several weeks to one year.

The terms "a", "an" and "one", as used herein, are meant to be interpreted as "one or more" and "at least one."

The term "stabilized", as used herein, refers to a significant improvement in the stability of the components in the injectable polymeric composition, which is necessary to achieve a stable state required to develop a viable product. The term "stabilized injectable polymeric composition" as used herein means that the components, e.g., the polymer and the peptide agent, of the composition retains at least 80%, preferably at least 90%, of their original molecular weight, structure and/or biological activity during manufacturing and after storage for an extended time period, e.g., months to years, preferably more than 12 months, under appropriate conditions.

The term "controlled release delivery", as defined herein, is intended to refer to the delivery of a peptide agent in vivo over a desired, extended period of time following administration, preferably from at least several weeks to one year.

The term "peptide agent" as used herein is in a generic sense to include poly(amino acids) that are normally generally referred to as "peptides", "oligopeptides", and "polypeptides" or "proteins" which are used interchangeably herein. The term also includes peptide agent analogs, derivatives, acylated derivatives, glycosylated derivatives, pegylated derivatives, fusion proteins and the like. The "basic peptide agent" is a peptide which is basic in nature, arising from the presence of basic amino acids, for example arginine or lysine, or arising from the N-terminus of the peptide agent, or simply a peptide agent which contains at least one basic group, optionally in the presence of one or more acidic amino acid groups. The term also includes synthetic analogues of peptides, unnatural amino acids having basic functionality, or any other form of introduced basicity.

The term "peptide agent" is meant to include any peptide agents having diagnostic and/or therapeutic properties including, but not limited to, antimetabolic, antifungal, anti-inflammatory, antitumoral, antiinfectious, antibiotics, nutrient, agonist, and antagonist properties.

Specifically, the peptide agents of the invention may be any peptides capable of forming a beneficial salt with a strong acid, in particular a peptide agent containing an electron donor base group such as a basic nitrogen atom, e.g. an amine, imine or ring nitrogen. The peptide agents preferably contain one or more exposed protonatable amine functionalities. Peptide agents useful in the preparation of the compositions of the present invention include, but are not limited to, oxytocin, vasopressin, adrenocorticotropic hormone (ACTH), epidermal growth factor (EGF), platelet-derived growth factor (PDGF), prolactin, luteinising hormone, luteinizing hormone releasing hormone (LHRH), LHRH agonists, LHRH antagonists, growth hormones (including human, porcine, and bovine), growth hormone releasing factor, insulin, erythropoietin (including all proteins with erythropoietic activity), somatostatin, glucagon, interleukin (which includes IL-2, IL-11, IL-12, etc.), interferon-alpha, interferon-beta, interferon-gamma, gastrin, tetragastrin, pentagastrin, urogastrone, secretin, calcitonin, enkephalins, endorphins, angiotensins, thyrotropin releasing hormone (TRH), tumor necrosis factor (TNF), parathyroid hormone (PTH), nerve growth factor (NGF), granulocyte-colony stimulating factor (G-CSF), granulocyte macrophage-colony stimulating factor (GM-CSF), macrophage-colony stimulating factor (M-CSF), heparinase, vascular endothelial growth factor (VEG-F), bone morphogenic protein (BMP), hANP, glucagon-like peptide (GLP-1), exenatide, peptide YY (PYY), renin, bradykinin, bacitracins, polymyxins, colistins, tyrocidine, gramicidins, cyclosporins (which includes synthetic analogues and pharmacologically active fragments thereof), enzymes, cytokines, antibodies, vaccines, antibiotics, antibodies, glycoproteins, follicle stimulating hormone, kyotorphin, taftsin, thymopoietin, thymosin, thymostimulin, thymic humoral factor, serum thymic factor, colony stimulating factors, motilin, bombesin, dinorphin, neurotensin, cerulein, urokinase, kallikrein, substance P analogues and antagonists, angiotensin II, blood coagulation factor VII and IX, gramicidines, melanocyte stimulating hormone, thyroid hormone releasing hormone, thyroid stimulating hormone, pancreozym in, cholecystokinin, human placental lactogen, human chorionic gonadotrophin, protein synthesis stimulating peptide, gastric inhibitory peptide, vasoactive intestinal peptide, platelet derived growth factor, and synthetic analogues and modifications and pharmacologically-active fragments thereof.

The preferred peptide agents used herein include the peptide agents wherein the N-terminus is not a primary amine. For example, the N-terminus of the peptide agents may be a pyroglutamic acid, e.g., LHRH, and LHRH agonists such as leuprorelin, buserelin, gonadorelin, deslorelin, fertirelin, histrelin, lutrelin, goserelin, nafarelin, triptorelin, and the like. Alternatively, the N-terminal amine group may be capped or acylated, e.g., cetrorelix, enfuvirtide, thymosin a abarelix, and the Ike The preferred peptide agents used herein also include the peptide agents wherein the N-terminal primary amine is covalently modified with hydrophilic and/or lipophilic moieties such as through pegylation, acylation, and the like. The peptide agents used herein further include the peptide agents wherein the side chain primary amine(s) are covalently modified with hydrophilic and/or lipophilic moieties such as through pegylation, acylation, and the like. The preferred peptide agents used herein further include the peptide agents wherein both N-terminal primary amine and side chain primary amine groups are covalently modified simultaneously with hydrophilic and/or lipophilic moieties such as through pegylation, acylation, and the like.

The term "hydrophilic moiety" refers to any water-soluble linear or branched oligomer or polymer including, but not limited to, polyethylene glycol and polypropylene glycol and similar linear and branched polymers. Preferably, the molecular weight of the polymer ranges from about 500 daltons to about 50,000 daltons. Hydrophilic polymers for use in the present invention may have a reactive group incorporated for attachment to the peptide agent of interest through amine, carboxylic, hydroxyl, or thiol groups.

The term "pegylation" used herein refers to the covalent conjugation of a soluble polyethylene glycol to the peptide agents. Polyethylene glycol can be prepared according to standard protocols with one end capped as with a methoxy group and the other end activated for facile conjugation to active groups on peptide agents. For examples, various methods for preparing polyethylene glycols and their use for pegylations are described in the art: [e.g., Roberts M J, Bentley M D, Harris J M, Chemistry for peptide and protein PEGylation. Adv Drug Deliv Rev. 2002 Jun. 17; 54(4): 459-76. Veronese F M. Peptide and protein PEGylation: a review of problems and solutions. Biomaterials. 2001 March; 22(5): 405-17 and U.S. Pat. Nos. 6,113,906; 5,446, 090; 5,880,255], which are all incorporated herein by reference.

The term "lipophilic moiety" refers to any molecules having a solubility in water at 20° C. less than 5 mg/ml, preferably less than 0.5 mg/ml, more preferably less than 0.1 mg/mL. Such a lipophilic moiety is preferably selected from $C_{2-39}$-alkyl, $C_{2-39}$-alkenyl, $C_{2-39}$-alkadienyl and steroidal residues. The term "$C_{2-39}$-alkyl, $C_{2-39}$-alkenyl, $C_{2-39}$-alkadienyl" are intended to cover straight chain and branched, preferably straight chain, saturated, monounsaturated and di-unsaturated hydrocarbon of 2-39 carbon atoms.

Introduction of a lipophilic moiety covalently to a peptide agent thereof leads to a lipophilically modified peptide that may have improved therapeutic effect comparing to the native molecule. This can be typically done by reacting an amine group in a peptide agent with an acid or other reactive groups in a lipophilic molecule. Alternatively, the conjugation between peptide agent and lipophilic molecule is accomplished through an additional moiety such as a bridge, spacer, or linkage moiety, which can be degradable or non-degradable. Some examples are disclosed in the prior art, [e.g., Hashimoto, M., et al., Pharmaceutical Research, 6:171-176 (1989), and Lindsay, D. G., et al., Biochemical J. 121:737-745 (1971), U.S. Pat. No. 5,693,609, WO95/07931, U.S. Pat. No. 5,750,497, and WO96/29342. WO98/08871, WO98/08872, and WO99/43708]. These disclosures are expressly incorporated herein by reference for describing lipophilically modified peptides and for enabling preparation of the same.

The term "strong acid", as defined herein, is meant to include any acids with a pKa less than 3, preferably less than 0, and more preferably less than −3. The strong acids suitable for the present invention may be selected from, but not limited to, the group consisting of hydrochloric acid, hydrobromic acid, nitric acid, chromic acid, sulfuric acid, methanesulfonic acid, trifluromethane sulfonic acid, trichloroacetic acid, dichloroacetic acid, bromoacetic acid, chloroacetic acid, cyanoacetic acid, 2-chloropropanoic acid, 2-oxobutanoic acid, 2-chlorobutanoic acid, 4-cyanobutanoic acid, pamoic acid, perchloric acid, phosphoric acid, hydrogen iodide, and the like.

The "strong acid" of the present invention also includes any organic sulfuric acids such as alkyl, aryl or alkylaryl sulfuric acids of 1-40 carbons, preferably less than 18 carbons, and more preferably less than 6 carbons, and organic sulfonic acids such as alkane, arylalkane, arene, or alkene sulfonic acids of 1-40 carbons, preferably less than 18 carbons, and more preferably less than 6 carbons.

The term "a beneficial salt of a peptide agent", as defined herein, is meant to include any salts of a peptide agent formed with a strong acid. The beneficial salts of peptide agents can be prepared by simple acid and base titration or neutralization. The beneficial salts of peptide agents can be prepared during its synthesis and purification processes. Alternatively, they can be prepared from peptide agent in the form of a free base. The free base is dissolved in a suitable liquid medium. This solution of the peptide agent is mixed with a solution of a strong acid to form the beneficial salts by removing the solvent through suitable means such as filtration or lyophilization. If the peptide agent is in its common commercially available form of a salt formed with a weak acid (i.e., pKa>3), the weak acid can be replaced by a strong acid through common ion-exchange methods such as lyophilization, precipitation or other methods known in the art. For example, leuprolide acetate is dissolved in a suitable liquid medium, e.g., water. This solution of the peptide agent is mixed with an aqueous solution of a strong acid such as hydrochloric acid. When the peptide acetate and a strong acid such as hydrochloric acid are dissolved in water, the peptide tends to be associated with chloride ion, as the stronger acid HCl displaces the weaker carboxylic acetic acid. The solvent and liberated acetic acid (or other weak but volatile carboxylic acid) may be removed under vacuum. Thus, the mixture solution is freeze-dried to remove water and weaker acid to form the beneficial salts. If the peptide agent is not stable under low pH, the beneficial salts of the peptide agent can be prepared through extensive dialysis against very low concentration of a strong acid.

The injectable polymeric compositions of the present invention may contain peptide agent in a range of 0.01 to 40% by weight. In general, the optimal drug loading depends upon the period of release desired and the potency of the peptide agent. Obviously, for peptide agent of low potency and longer period of release, higher levels of incorporation may be required.

The term "biodegradable" refers to a material that gradually decomposes, dissolves, hydrolyzes and/or erodes in situ. Generally, the "biodegradable polymers" herein are polymers that are hydrolyzable, and/or bioerode in situ primarily through hydrolysis and/or enzymolysis.

The term "biodegradable polymer" as used herein is meant to include any biocompatible and/or biodegradable synthetic and natural polymers that can be used in vivo, provided the polymer is at least substantially insoluble in aqueous medium or body fluid. The term "substantially insoluble" as used herein refers that the insolubility of the polymer must be sufficient to result in precipitation of the polymer in aqueous medium or body fluid. Preferably, the solubility of the polymers is less than 1% by weight, and more preferably less than 0.1%. When the polymer solution in a water miscible or dispersible organic solvent is mixed with an aqueous solution, the polymer will precipitate to form a solid or gelled matrix as the organic solvent dissipates. Suitable biodegradable polymers are disclosed, e.g., in U.S. Pat. Nos. 4,938,763; 5,278,201; 5,278,2012; U.S. Pat. Nos. 5,324,519; 5,702,716; 5,744,153; 5,990,194; and 6,773,714. Some non-limiting examples of the polymers are polylactides, polyglycolides, polycaprolactones, polydioxanones, polycarbonates, polyhydroxybutyrates, polyalkylene oxalates, polyanhydrides, polyesteram ides, polyurethanes, polyacetals, polyorthocarbonates, polyphosphazenes, polyhydroxyvalerates, polyalkylene succinates, poly(malic acid), and polyorthoesters, and copolymers, block copolymers, branched copolymers, terpolymers and combinations and mixtures thereof.

The block copolymers include A-B-A block copolymers, B-A-B block copolymers, and/or A-B block copolymers and/or branched copolymers. The preferred block copolymers are those wherein the A block comprises a hydrophobic polymer and the B block comprises a hydrophilic polymer. Particularly, when using one of the aforementioned block copolymers, the most preferred polymeric matrices are defined where the A block is a biodegradable polymer selected from the group consisting of polylactides, polyglycolides, poly(lactide-co-glycolide)s, polyanhydrides, poly (ortho ester)s, polyetheresters, polycaprolactones, polyesteramides, poly(ε-caprolactone)s, poly(hydroxybutyric acid)s, and blends and copolymers thereof, and the B block is polyethylene glycol or monofunctionally derivatized polyethylene glycol such as methoxy polyethylene glycol. Many of these combinations may form acceptable thermal reversible gels.

Suitable molecular weights for polymers may be determined by a person of ordinary skill in the art. Factors that may be considered when determining molecular weights include desired polymer degradation rate, mechanical strength, and rate of dissolution of polymer in organic solvents. Typically, a suitable range of weight averaged molecular weights of polymers is of about 2,000 Daltons to about 100,000 Daltons with a polydispersity of from 1.1 to 2.5, depending upon which polymer is selected for use, among other factors.

The injectable polymeric compositions of the present invention may contain biodegradable polymer in a range of 10% to 70% by weight. The viscosity of the injectable compositions of the invention depends on the molecular weight of the polymer and organic solvent used. Typically, when the same solvent is used, the higher the molecular weight and the concentration of the polymer, the higher the viscosity. Preferably the concentration of the polymer in the compositions is less than 70% by weight. More preferably concentration of the polymer in the compositions is between 30 to 60% by weight.

Poly(lactic acid), and copolymers of lactic acid and glycolic acid (PLGA), including poly(D,L-lactide-co-glycolide) and poly(L-lactide-co-glycolide) are preferably used in the present invention. The polymers (or thermoplastic polyesters) have monomer ratios of lactic acid to glycolic acid of between about 50:50 to about 100:0 and weight average molecular weights of between about 2,000 to about 100,000. The biodegradable thermoplastic polyesters can be prepared using the methods known in the art, e.g., polycondensation and ring-opening polymerization (e.g., U.S. Pat. Nos. 4,443,340; 5,242,910; 5,310,865, which are all incorporated herein by reference). The terminal groups of the poly(DL-lactide-co-glycolide) can either be hydroxyl, carboxylic, or ester depending upon the method of polymerization. The suitable polymers may include a monofunctional alcohol or a polyol residue and may not have a carboxylic acid terminus. Examples of monofunctional alcohols are methanol, ethanol, or 1-dodecanol. The polyol may be a diol, triol, tetraol, pentaol and hexaol including ethylene glycol, 1,6-hexanediol, polyethylene glycol, glycerol, saccharides, reduced saccharides such as sorbitol, and the like.

Many suitable PLGAs are available commercially, and the PLGAs of specific compositions can be readily prepared according to the prior art. The PLGAs of various monomer ratios and molecular weights are available from Boehringer-Ingelheim (Petersburg, Va., USA), Lakeshore Biomaterials (Birmingham, Ala., USA), DURECT Corporation (Pelham, Ala.).

The type, molecular weight, and amount of biodegradable polymer present in the compositions can influence the length of time in which the peptide agent is released from the controlled release implant. The selection of the type, molecular weight, and amount of biodegradable polymer present in the compositions to achieve desired properties of the controlled release implant can be determined by simple experimentations.

In one preferred embodiment of the present invention, the liquid composition can be used to formulate a controlled release delivery system for leuprolide hydrochloride. In such an embodiment, the biodegradable thermoplastic polyester can preferably be 85/15 poly (DL-lactide-co-glycolide) containing a hydroxyl terminal group and a lauryl ester terminus; can be present in about 30% to about 60% of the composition by weight; and can have an average molecular weight of about 15,000 to about 50,000.

In another preferred embodiment of the present invention, the liquid composition can be used to formulate a controlled release delivery system for leuprolide hydrochloride. In such an embodiment, the biodegradable thermoplastic polyester can preferably be 85/15 poly (DL-lactide-co-glycolide) containing two hydroxyl terminal groups; can be present in about 30% to about 60% of the composition by weight; and can have an average molecular weight of about 15,000 to about 50,000.

In still another preferred embodiment of the present invention, the liquid composition can be used to formulate a controlled release delivery system for leuprolide hydrochloride. In such an embodiment, the biodegradable thermoplastic polyester can preferably be 85/15 poly (DL-lactide-co-glycolide) containing a carboxylic acid terminal groups; can be present in about 30% to about 60% of the composition by weight; and can have an average molecular weight of about 15,000 to about 50,000.

In still another preferred embodiment of the present invention, the composition can be used to formulate a controlled release delivery system of leuprolide. In such an embodiment, the biodegradable polymer can preferably be 100/0 poly (DL-lactide) with/without carboxylic acid terminal groups; can be present in about 40% to about 60% of the composition by weight; and can have an average molecular weight of about 8,000 to about 50,000.

The term "pharmaceutically acceptable organic solvent" is meant to include any biocompatible organic solvents that are miscible or dispersible in aqueous or body fluid. The term "dispersible" means that the solvent partially soluble or miscible in water. Preferably, a single solvent or a mixture of solvents has a solubility or miscibility in water of greater than 0.1% by weight. More preferably, the solvent has a solubility or miscibility in water of greater than 3% by weight. Most preferably, the solvent has a solubility or miscibility in water of greater than 7% by weight. The suitable organic solvent should be able to diffuse into body fluid so that the liquid composition coagulates or solidifies. Single and/or mixture of such solvents can be employed; the suitability of such solvents can be determined readily by simple experimentations.

Examples of pharmaceutically acceptable organic solvent include, but not limited to, N-methyl-2-pyrrolidone, methoxypolyethylene glycol, alkoxypolyethylene glycol, polyethylene glycol esters, glycofurol, glycerol formal, methyl acetate, ethyl acetate, methyl ethyl ketone, dimethylformamide, dimethyl sulfoxide, tetrahydrofuran, caprolactam, decylmethylsulfoxide, benzyl benzoate, ethyl benzoate, triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, ethyl lactate, propylene carbonate, ethylene carbonate, butyrolactone, and 1-dodecylazacyclo-heptan-2-one, and combinations thereof.

The solubility of the biodegradable polymers in various pharmaceutically acceptable organic solvents will differ depending upon the characteristics of the polymers and their compatibility with various solvents. Thus, the same polymer will not be soluble to the same extent in different solvents. For example, PLGA has a much higher solubility in N-methyl-2-pyrrolidone (NMP) than that in triacetin. However, when PLGA solution in NMP is in contact with aqueous solution, NMP will dissipate very rapidly to form a solid polymer matrix due to its high water miscibility. The fast diffusion rate of the solvent may result in a solid implant quickly, however, it may also lead to a high initial burst release. When PLGA solution in triacetin is in contact with aqueous solution, triacetin will dissipate very slowly due to its low water miscibility. The slow diffusion rate of the solvent may take a long time to transform from a viscous liquid to a solid matrix. There may be an optimum balance at which the solvent diffuse out and the coagulation of the polymer to encapsulate peptide agents. Therefore, it may be advantageous to combine different solvents to obtain a desirable delivery system. The solvents of low and high water miscibility may be combined to improve the solubility of the polymer, modify the viscosity of the composition, optimize the diffusion rate, and reduce the initial burst release, The injectable polymeric compositions of the present invention typically contain an organic solvent in a range of 30% to 80% by weight. The viscosity of the injectable compositions of the invention depends on the molecular weight of the polymer and organic solvent used. Preferably the concentration of the polymer in the compositions is less than 70% by weight. More preferably concentration of the polymer in solutions is between 30 to 60% by weight.

The term "excipients" as used herein is meant to include any useful ingredient in the composition aside from the peptide agent or the biodegradable polymers used to form the composition. Suitable excipients include release rate modifying agents, burst effect reducing materials, buffering materials, antioxidants, and the like.

According to the present invention, suitable release rate modifying agents include, but not limited to, amphiphilic compounds or copolymers, such alkanecarboxylic acid, oleic acid, alkyl alcohol, polar lipids, surfactants, copolymers of polyethyleneglycol and polylactide or poly(lactide-co-glycolide), poloxamers, polyvinylpyrrolidone, polysorbates, and the like; esters of mono-, di-, and tricarboxylic acids, such as 2-ethoxyethyl acetate, triethyl citrate, acetyl tributyl citrate, acetyl triethyl citrate, glycerol triacetate, di(n-butyl) sebecate, and the like; polyhydroxy alcohols, such as polyethylene glycol, sorbitol, and the like; fatty acids; triesters of glycerol, such as triglycerides, medium-chain triglycerides such as MIGLYOL 810, 812, 818, 829, 840, and the like. Mixtures of rate modifying agents can also be used in the polymer systems of the invention.

The release rate modifying agents may be present in the injectable polymeric composition in an amount effective to reduce the initial burst of peptide agent released from the polymeric composition during the first 24 hours after implantation. Preferably, the polymeric composition includes about 1% to about 50% by weight, more preferably about 2% to about 20% by weight of the release rate modifying agents.

According to the present invention, suitable buffering agents include, but are not limited to, inorganic and organic salts including calcium carbonate, calcium hydroxide, calcium myristate; calcium oleate, calcium palmitate, calcium stearate, calcium phosphate, magnesium carbonate, magnesium hydroxide, magnesium phosphate, magnesium myristate, magnesium oleate, magnesium palmitate, magnesium stearate, zinc carbonate, zinc hydroxide, zinc myristate, zinc oleate, zinc palmitate, zinc stearate, zinc phosphate, and combinations thereof.

The buffering agents may be present in the injectable polymeric composition in an amount effective to stabilize the pH within the implants during the degradation process. Preferably, the polymeric composition includes about 1 wt % to about 30 wt %, more preferably about 2 wt % to about 15 wt % of the buffering agents.

According to the present invention, suitable antioxidants include, but are not limited to, d-alpha tocopherol acetate, ascorbyl palmitate, butylated hydroxyanidole, butylated hydroxyanisole, butylatedhydroxyquinone, hydroxycomarin, butylated hydroxytoluene, ethyl gallate, propyl gallate, octyl gallate, lauryl gallate, propylhydroxybenzoate, trihydroxybutylrophenone, vitamin E, pegylated vitamin E or vitamin E-TPGS, and the like.

The antioxidants may be present in the injectable polymeric composition in an amount effective to scavenge any radicals or peroxides generated within the implants. Preferably, the polymeric composition includes about 1 wt % to about 30 wt %, more preferably about 3 wt % to about 15 wt % of the antioxidants.

In one aspect the present invention provides a stabilized injectable biodegradable polymeric composition for forming an economical, practical, and efficient controlled release delivery system for peptide agents comprises a) a beneficial salt of a peptide agent formed with a strong acid which minimizes or prevents the interaction/reaction between the peptide agent and the polymer in an organic solution; b) a biodegradable polymer; c) a pharmaceutically acceptable organic solvent; and d) optionally one or more excipients to achieve optimal delivery of the peptide agent. Preferably, the injectable composition is packaged into a kit comprising a step to fill the composition into a syringe in a ready-to-use configuration. The composition in the kit is stable for a reasonable period of time, preferably at least one year, to have a suitable storage shelf-life under controlled storage conditions. The composition is preferably injected into a subject to form in situ an implant, from which the peptide agent is released in a therapeutic effective amount over a desired, extended period of time.

The stabilized injectable biodegradable polymeric composition of the present invention can be prepared by appropriately combining a beneficial salt of a peptide agent, a biodegradable polymer, a pharmaceutically acceptable organic solvent, and an optional excipient. The composition for administration may conveniently presented in dosage unit form and may be prepared by any of the methods known in the art of pharmacy. One preferred method of preparing the composition of the present invention is to dissolve a biodegradable polymer and/or an excipient in a pharmaceutically acceptable organic solvent to obtain a uniform polymer solution/suspension first. Then the beneficial salt of a peptide agent is added to this solution/suspension. The components are thoroughly mixed using any proper means to obtain a uniform solution or suspension. Then an appropriate amount of the solution or suspension is transferred into a syringe to obtain a ready-to-use product.

The level of incorporation of the beneficial salt and polymer in the composition of the invention will naturally vary, depending upon the potency of the peptide agent component, the period of time over which delivery of the agent is desired, the solubility of the polymer in the solvent, and the volume and viscosity of the injectable composition which is desired to administer.

In certain preferred embodiments of the present invention, the injectable biodegradable polymeric composition for forming an economical, practical, and efficient controlled release delivery system for peptide agents contains about 0.01% to 40% of the beneficial salt of a peptide agent and about 10% to 70% of a poly(lactide-co-glycolide) polymer. The composition further contains about 30% to 70% of a pharmaceutically acceptable organic solvent.

In a preferred embodiment of the present invention, the composition further contains about 1% to 40% of a suitable excipient including release rate modifying agents, burst effect reducing materials, buffering materials, antioxidants, tissue transporting agents and the like as defined above.

According to the present invention, the injectable composition is transferred into a sterile container suitable for injection administration, e.g., a syringe. The container is packaged for storage and the components of the composition retains at least 80%, preferably 90%, of their original molecular weight, structure and/or biological activity during manufacturing and storage processes or prior to administration to a subject such as an animal or human.

Thus, according to the present invention, the stabilized compositions can be administered to a subject where controlled release delivery of a peptide agent is desired. As used herein, the term "subject" is intended to include warm-blooded animals, preferably mammals, most preferably humans.

As used herein, the term "administered to a subject" is intended to refer to dispensing, delivering or applying a composition (e.g., pharmaceutical formulation) to a subject by any suitable route for delivery of the composition to the desired location in the subject. Preferably, the composition of the present invention can be administered by injection and/or implantation subcutaneously, intramuscularly, intraperitoneally, or intradermally to provide the desired dosage based on the known parameters for treatment of the various medical conditions with the peptide agent.

The term "controlled release delivery", as defined herein, is intended to refer to continual delivery of a peptide agent in vivo over a period of time following administration, preferably from at least several weeks to one year. Sustained controlled release delivery of the agent can be demonstrated by, for example, the continued therapeutic effect of the agent over time (e.g., for an LHRH analogue, sustained delivery of the analogue can be demonstrated by continued suppression of testosterone synthesis over time). Alternatively, sustained delivery of the peptide agent may be demonstrated by detecting the presence of the agent in vivo over time.

The amount of the injectable composition administered will typically depend upon the desired properties of the controlled release implant. For example, the amount of the injectable composition can influence the length of time in which the peptide agent is released from the controlled release implant.

In a preferred embodiment, the volume of the injectable polymeric composition of the present invention to be injected to a subject ranges from 0.1 mL to 2.0 mL; preferably from 0.2 mL to 1.0 mL; and more preferably from 0.3 mL to 0.5 mL.

The present invention further provides a method for in situ forming an implant in a subject comprising administering to a subject an effective amount of the injectable composition comprising: a) a beneficial salt of a peptide agent formed with a strong acid which minimizes or prevents the interaction/reaction between the peptide agent and the polymer in an organic solution; b) a biodegradable polymer; c) a pharmaceutically acceptable organic solvent; and d) optionally one or more excipients to achieve optimal delivery of the peptide agent; and allowing the solvent to dissipate into the surrounding aqueous environment to transform the liquid composition into a depot by phase separation. The depot may be a viscous gel, a semi-solid, or a solid matrix. The depot may also be porous or non-porous. The depot serves as the delivery system from which the peptide agent is released over a desired and extended period of time.

In another preferred embodiment, the injectable composition of the present invention may be administered to fit into a body cavity to form a depot system. Such cavities include the cavities created after a surgery or natural body cavity such as vagina, anus, and the like.

In another aspect, the present invention provides a stabilized liquid biodegradable polymeric composition for forming an economical, practical, and efficient controlled release delivery system for peptide agents comprises a) a beneficial salt of a peptide agent formed with a strong acid which minimizes or prevents the interaction/reaction between the peptide agent and the polymer in an organic solution; b) a biodegradable polymer; c) an organic solvent; and d) optionally one or more excipients to achieve optimal delivery of the peptide agent. The liquid biodegradable polymeric composition may be fabricated into implantable polymeric matrices. Wherein the liquid biodegradable polymeric composition retains at least 90%, preferably 95%, of their original molecular weight, structure and/or biological activity before and during the fabrication process.

As used herein, the term of "implantable polymeric matrices" is intended to include particles, films, pellets, cylinders, discs, microcapsules, microspheres, nanospheres, microparticles, wafers, and other known polymeric configurations used for drug delivery.

Methods for forming various pharmaceutically acceptable polymer carriers are well known in the art. For examples, various methods and materials are described in U.S. Pat. Nos. 6,410,044; 5,698,213; 6,312,679; 5,410,016; 5.529,914; 5,501,863; and PCT Publication No. WO 93/16687; U.S. Pat. Nos. 4,938,763; 5,278,201; 5,278,202; EP 0,058,481; which are all incorporated herein by reference.

According to the present invention, the implantable polymeric matrices in the form of microspheres are produced by encapsulating the beneficial salt of peptide agents into the polymer. The beneficial salt of peptide agents can be encapsulated using various biocompatible and/or biodegradable polymers having unique properties that are suitable for delivery to different biological environments or for effecting specific functions. The rate of dissolution and, therefore, delivery of peptide agent is determined by the particular encapsulation technique, polymer composition, polymer crosslinking, polymer thickness, polymer solubility, size and solubility of biologically active compound/polyanion complex.

The beneficial salts of peptide agents to be encapsulated are dissolved or suspended in a polymer solution in an organic solvent. The polymer solution must be concentrated enough to completely coat the beneficial salt after they are added to the solution. Such an amount is one that provides a weight ratio of the beneficial salt of peptide agents to polymer between about 0.01 and about 50, preferably between about 0.1 and about 30. The beneficial salt of peptide agents should be kept suspended and not allowed to aggregate as they are coated by contact with the polymer.

A polymer solution of the beneficial salts of peptide agents can therefore be subjected to a variety of microencapsulation techniques including spray drying, spray congealing, emulsion, and solvent evaporation emulsion.

According to one embodiment of the invention, the beneficial salt of peptide agents is dissolved or suspended in a polymer solution in an organic solvent. The solution or suspension is transferred to a larger volume of an aqueous solution containing an emulsifier. In the aqueous solution, the organic phase is emulsified, where the organic solvent evaporates or diffuses away from the polymer. The solidified polymer encapsulates the beneficial salt of peptide agents to form a polymer matrix. The emulsifier helps to reduce the interfacial surface tension between the various phases of matter in the system during the hardening phase of the process. Alternatively, if the encapsulating polymer has some inherent surface activity, there may be no need for addition of a separate surface-active agent.

Emulsifiers useful to prepare encapsulated the beneficial salt of peptide agents according to the present invention include poloxamers and polyvinyl alcohol as exemplified herein, surfactants and other surface active compounds which can reduce the surface tension between the polymer encapsulated beneficial salt of peptide agents and the solution.

Organic solvents useful to prepare the microspheres of the present invention, except for those disclosed above, also include acetic acid, acetone, methylene chloride, ethyl acetate, chloroform and other non-toxic solvents that will depend on the properties of the polymer. Solvents should be chosen to dissolve the polymer and are ultimately non-toxic.

Thus, according to the present invention, these implantable polymeric matrices can be administered to a subject where sustained controlled release delivery of a peptide agent is desired. Preferably, the implantable polymeric matrices of the invention can be administered by injection and/or implantation subcutaneously, intramuscularly, intraperitoneally, or intradermally to provide the desired dosage based on the known parameters for treatment of the various medical conditions with the peptide agent.

All books, articles and patents referenced herein are fully incorporated by reference.

EXAMPLES

The following examples illustrate the compositions and methods of the present invention. The following examples should not be considered as limitations, but should merely teach how to make the useful controlled release drug delivery compositions.

Example 1

Preparation of Beneficial Salts of Peptide Agents and Peptide Derivatives Formed with Strong Acids Peptide agent or peptide derivative containing at least one basic functional group is dissolved in water. Stoichiometric amounts of a strong acid are added to the aqueous solution of the peptide agent, resulting in neutralization of the basic groups in the peptide agent. The salt is obtained by precipitation, filtration and/or lyophilization.

Example 2

Preparation of Leuprolide Hydrochloride

Leuprolide is a luteinizing hormone releasing hormone (LHRH) agonist containing 9 amino acid residues and two basic functionalities (a histidine and an arginine group). Its N-terminal amine was blocked in the form of pyroglutamic acid. It has been used in the treatment of prostate cancer and endometriosis. Leuprolide acetate (LA-Ac) was obtained from Polypeptides Laboratories, Inc. (PPL Lot#PPL-LEUPO401A). Leuprolide Hydrochloride (LA-HCl) was prepared by replacing acetic acid with HCl through an ion-exchange and lyophilization process. Typically, 1000 mg of leuprolide acetate was dissolved in 30 mL water. 3.19 mL of 0.5 N HCl (HCl:LA~2.2:1) was added and mixed well. The solution was freeze-dried for 72 h to remove acetic acid. The dried powder was re-dissolved in water and freeze-dried again.

Example 3

Preparation of Leuprolide Mesylate 343.5 mg of leuprolide acetate (PPL Lot#PPL-LEUPO401A) was dissolved in 20 mL water. 32 µL of methanesulfonic acid was added and mixed well (molar ratio of leuprolide acetate to methanesulfonic acid ~1:2). The solution was freeze-dried for 72 h to remove acetic acid. The dried powder was re-dissolved in water and freeze-dried again.

Example 4

Preparation of Goserelin Hydrochloride 766 mg of goserelin acetate (PPL Lot#0603-219) was dissolved in 20 mL water. 2.12 mL of 0.5 N HCl (molar ration of HCl:goserelin acetate~2.2:1) was added and mixed well. The solution was freeze-dried for 72 h to remove acetic acid. The dried powder was re-dissolved in water and freeze-dried again.

Example 5

Preparation of Palmitoyl-Octreotide (PAL-OCT)

50 mg of octreotide acetate was dissolved in 1000 uL of anhydrous DMSO containing 100 uL TEA. 17.1 mg of Palmitic acid N-hydroxysuccinimide ester (Mw 353.50) was dissolved in 3 mL anhydrous DMSO and added by direct injection to the peptide solution. The reaction was allowed to proceed for overnight at room temperature. The mixture was poured into diethyl ether to precipitate palmitoylated octreotide. The precipitate was washed with diethyl ether twice and then dried under vacuum. The resulting acylated peptide was in a form of white powder. The beneficial salt of the acylated peptide was formed by neutralizing the residual basic amine groups using a strong acid.

Example 6

Preparation of Decanal-Octreotide (DCL-OCT)

50 mg of octreotide was dissolved in 2 mL of 20 mM sodium cyanoborohydride (Mw 62.84, NaCNBH$_3$) (2.51 mg) solution in 0.1 M acetate buffer at pH 5. 13.7 mg of Decanal (Mw 156.27) (OCT:DCL=1:2) was added by direct injection to the peptide solution. The reaction was allowed to proceed for overnight at 4° C. The mixture was separated by centrifugation. The precipitated PAL-OCT was freeze-dried. The beneficial salt of the acylated peptide was formed by neutralizing the residual basic amine groups using a strong acid.

Example 7

Preparation of PEGylated Octreotide

A solution of octreotide acetate (10 mg/mL) in water was added to a vial containing 2 molar equivalent amount of succinimidyl propionate monomethoxy PEG (SPA-mPEG, MW 2000 dalton) in 0.1 M phosphate buffer at pH 7.4. The reaction was allowed to proceed with stirring at 4° C. overnight. Then the reaction mixture was separated by using reversed-phase HPLC (RP-HPLC) on C-18 (YMC ODS-A 4.6×250 mm, 5 um, Waters Corporation). The mobile phase consisted of 0.1% TFA in water (A) and CAN containing 0.1% TFA (B). The mobile phase was run with a linear gradient from 30 to 60% eluent B for 20 min at a flow rate of 1 ml/min and the UV absorbance of the elution was monitored at 215 nm. The elution fractions corresponding to respective peaks were collected separately, purged with nitrogen, and lyophilized.

Alternatively, site-specific PEGylation of octreotide can be obtained. A solution of octreotide acetate (10 mg/mL) in 20 mM sodium cyanoborohydride (NaCNBH$_3$) and 0.1 M acetate buffer at pH 5 was added to a vial containing 3 molar equivalent amount of monomethoxy PEG-propionaldehyde (ALD-mPEG, MW 2000 dalton) in water. The reaction was allowed to proceed with stirring at 4° C. overnight. Then the reaction mixture was separated by using reversed-phase HPLC (RP-HPLC) on C-18 (YMC ODS-A 5 μg, 4.6×250 mm, Waters Corporation). The mobile phase consisted of 0.1% TFA in water (A) and CAN containing 0.1% TFA (B). The mobile phase was run with a linear gradient from 30 to 60% eluent B for 20 min at a flow rate of 1 ml/min and the UV absorbance of the elution was monitored at 215 nm. The elution fractions corresponding to respective peaks were collected separately, purged with nitrogen, and lyophilized. The beneficial salt of the pegylated peptide is formed by neutralizing the residual basic amine groups using a strong acid.

Example 8

Stability of Peptide Agent and Biodegradable Polymer in Injectable Polymeric Compositions Poly(DL-lactide-co-glycolide) (PLGA) of an 85/15 ratio of lactide to glycolide (DLPLG85/15, IV: 0.28) with a lauryl ester end group was dissolved in N-methyl-2-pyrrolidone (NMP) to give a 50% solution by weight. The leuprolide salts were mixed with the PLGA solution in NMP to give a uniform injectable composition at ratios shown in the Table 1. The injectable compositions were filled into 1.2 mIL polypropylene syringes with luer-lock tips. Then the pre-filled syringes were sealed using luer-lock caps. The capped syringes were packaged in a container and sealed in a plastic bag under vacuum and then stored at 4° C. and room temperature (~22° C.) for up to 18 months. The injectable composition was sampled at 24 h, 1, 2, 3, 6, 12, and 18 month time points. Purity of leuprolide in the sample was determined by HPLC. Molecular weight of the polymer was determined by gel permeation chromatography (GPC) using polystyrene standards with known molecular weights.

TABLE 1

Injectable polymeric formulations tested

| Samples | Leuprolide Salt (mg) | DLPLG 8515/NMP (mg) | Drug load (%, w/w) |
|---|---|---|---|
| Blank | 0 | 1000 | 0 |
| LA-Ac | 50 | 890 | 5.3 |
| LA-MS | 54 | 960 | 5.3 |
| LA-HCl-1 | 106 | 940 | 10.1 |
| LA-HCl-2 | 41 | 730 | 5.3 |

It was surprisingly found that the use of hydrochloride and mesylate salts of leuprolide instead of acetate significantly reduced the degradation of leuprolide and polymer in PLGA solutions in NMP at both 4° C. and room temperature over time. Tables 2 and 3 showed the degradation of leuprolide in PLGA solutions in NMP at 4° C. and room temperature over time respectively. At 4° C., up to 23% of leuprolide was degraded in the polymeric composition containing leuprolide acetate, while less than 2% of leuprolide was degraded for those formulations containing leuprolide hydrochloride and leuprolide mesylate after 18 months. At room temperature, more than 35% degradation of leuprolide was observed for leuprolide acetate formulations, while only about 11% for leuprolide hydrochloride and leuprolide mesylate formulations after 12 months. In addition, at room temperature, the color change (from milky to yellow to rusty color) and phase separation were observed. The phase separation resulted in heterogeneous formulations and uneven degradation of the peptide and the polymer in the formulation. The heterogeneity of the formulations may be the cause for the fluctuation of the results obtained at various time points.

TABLE 2

Stability of Leuprolide in PLGA/NMP Formulation at 4° C.

| Time (M) | LA-AC | LA-HCl-1 | LA-MS |
|---|---|---|---|
| 0 | 100.0 | 100.0 | 100.0 |
| 1 | 89.3 | 100.0 | 100.0 |
| 3 | 100.0 | 100.0 | 100.0 |
| 6 | 94.1 | 100.0 | 100.0 |
| 12 | 88.2 | 100.0 | 98.9 |
| 18 | 76.9 | 98.5 | 98.3 |

TABLE 3

Stability of Leuprolide in PLGA/NMP Formulation at RT

| Time (M) | LA-AC | LA-HCl-1 | LA-HCl-2 | LA-MS |
|---|---|---|---|---|
| 0 | 100 | 100 | 100 | 100 |
| 1 | 75 | 99 | 100 | 95 |
| 2 | 78 | 98 | 97 | 97 |
| 3 | 86 | 100 | 100 | 100 |
| 6 | 87 | 99 | 100 | 99 |
| 12 | 65 | 89 | 89 | 89 |

Table 4 and 5 showed the changes of molecular weight of the polymer in different formulations. Comparing to blank control, the molecular weight of PLGA in leuprolide acetate formulation decreased more than 10% at 4° C. and more than 90% at room temperature after 6 months. The molecular weight of PLGA in leuprolide hydrochloride and leuprolide mesylate formulations was the same as that of the blank control at both 4° C. and RT even after 12 months. However, after 12 months, more than 90% of the polymer from both blank control and leuprolide hydrochloride and leuprolide mesylate formulations was degraded. The results indicate that the salts of leuprolide formed with strong acid such as HCl and methanesulfonic acid completely prevent the interaction/reaction between the peptide and PLGA in solution. While the weak acid such as acetic acid does not prevent the deleterious interaction/reaction between the peptide and PLGA in solution. Thus, the improvement of the stability of the formulation by using the salt of the peptide formed with a strong acid enables the manufacturing of a ready-to-use injectable composition with a satisfactory storage stability of at least one year.

TABLE 4

Molecular Weight of PLGA in Different Formulations over time at 4° C.

| Time (M) | Blank | LA-AC | LA-HCl-1 | LA-MS |
|---|---|---|---|---|
| 0 | 24655 | 23842 | 24369 | 24556 |
| 1 | 25214 | 24282 | 25203 | 24574 |
| 3 | 24567 | 22775 | 24833 | 24833 |
| 6 | 23935 | 21957 | 24661 | 24034 |
| 12 | 23905 | 18906 | 23837 | 23393 |
| 18 | 22178 | 16107 | 22802 | 22227 |

TABLE 5

Molecular Weight of PLGA in Different Formulations over time at room temperature

| Time (M) | Blank | LA-AC | LA-HCl-1 | LA-HCl-2 | LA-MS |
|---|---|---|---|---|---|
| 0 | 24655.0 | 24282 | 24567 | 24468 | 24468 |
| 1 | 24282.2 | 20526 | 25022 | 25022 | 24832 |
| 2 | 22969.3 | 15459 | 23230 | 23230 | 22969 |
| 3 | 23227.7 | 11073 | 23228 | 23311 | 21872 |
| 6 | ND | 3409 | 18998 | 17952 | 15114 |
| 12 | 3112.3 | 380 | 4236 | 3388 | 2531 |

Example 9

Stability of Leuprolide and Polymer in Injectable Polymeric Compositions

Poly(DL-lactide-co-glycolide) (PLGA) of an 85/15 ratio of lactide to glycolide (DLPLG85/15, IV: 0.28) with a lauryl ester end group was dissolved in dimethylsulfoxide (DMSO) to give a 50% solution by weight. The leuprolide salts were mixed with the PLGA solution in DMSO to give a uniform injectable composition at ratios shown in the Table 6. The injectable compositions were filled into 1.2 mIL polypropylene syringes with luer-lock tips. Then the pre-filled syringes were sealed using luer-lock caps. The capped syringes were packaged in a container and sealed in a plastic bag under vacuum and then stored at 4° C. and room temperature (~22° C.) for up to 16 months. The injectable composition was sampled at pre-defined time points. Purity of leuprolide in the sample was determined by HPLC. Molecular weight of the polymer was determined by gel permeation chromatography (GPC) using polystyrene standards with known molecular weights.

TABLE 6

Injectable polymeric compositions tested

| Samples | Leuprolide Salt (mg) | DLPLG 8515 in DMSO (mg) | Drug load (%, w/w) |
|---|---|---|---|
| Blank | 0 | 4000 | 0 |
| LAAc | 200.4 | 4788 | 4 |
| LAMS-3 | 200.0 | 4806 | 4 |
| LAHCl-3 | 202.8 | 4810 | 4 |

Figure 1:
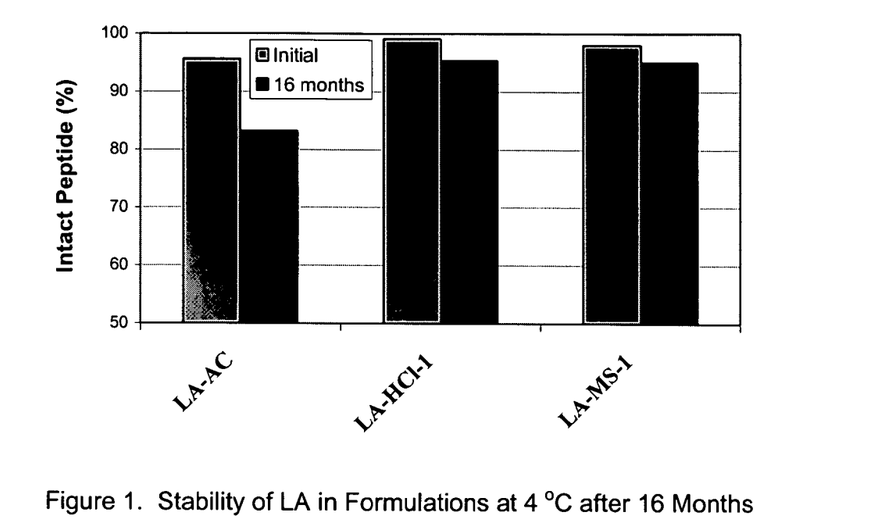
FIG. 1. Stability of LA in Formulations at 4° C. after 16 Months
Figure 2:
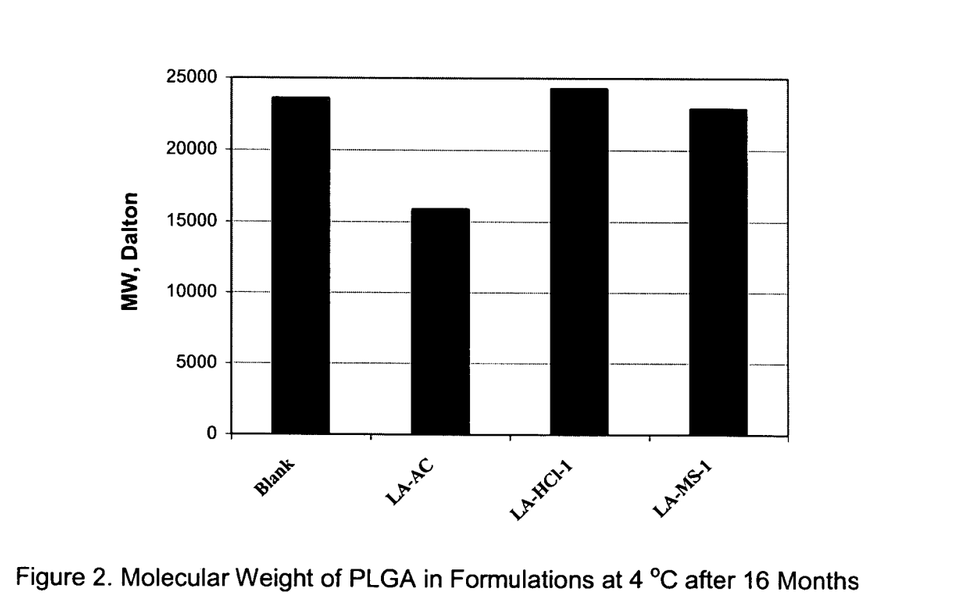
FIG. 2. Molecular Weight of PLGA in Formulations at 4° C. after 16 Months
Figure 5:
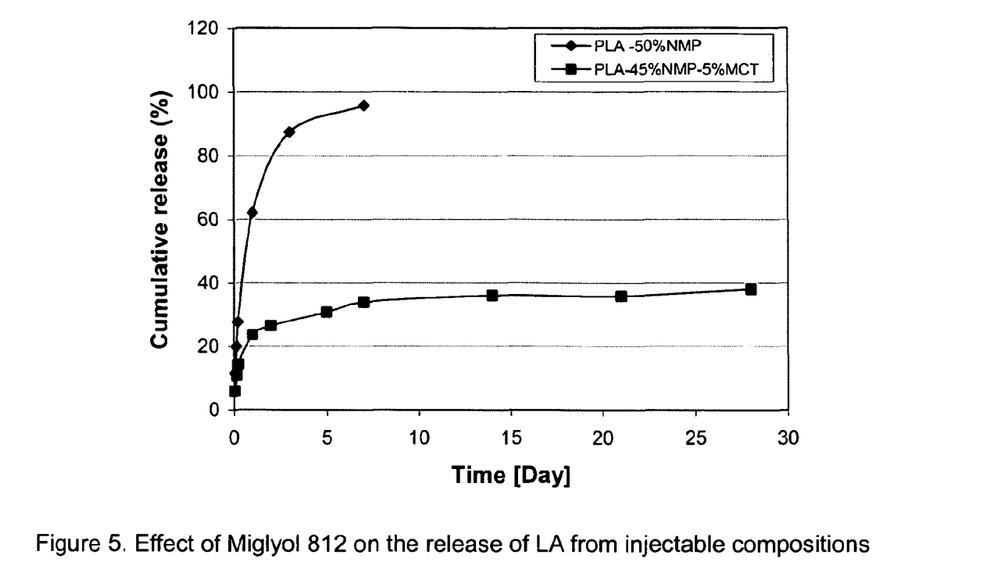
FIG. 5. Effect of Miglyol 812 on the release of LA from injectable compositions

It was surprisingly found that the use of hydrochloride and mesylate salts of leuprolide instead of acetate significantly reduced the degradation of leuprolide and polymer in PLGA solutions in DMSO at 4° C. over time. FIGS. 1 and 2 showed the degradation of leuprolide in PLGA in solutions in DMSO at 4° C. over time. Up to about 20% of leuprolide was degraded in the case of leuprolide acetate, while less than 5% of leuprolide was degraded for leuprolide hydrochloride and leuprolide mesylate formulations after 16 months. FIG. 5 showed the changes of molecular weight of PLGA in different formulations. Comparing to blank control, the molecular weight of PLGA in leuprolide acetate formulation decreased about 40% at 4° C. after 16 months. The molecular weight of PLGA in injectable polymeric compositions containing leuprolide hydrochloride and leuprolide mesylate was comparable to that of the control at 4° C. after 16 months. The results indicate that the salts of leuprolide formed with strong acid such as HCl and methanesulfonic acid almost completely prevent the interaction/reaction between the peptide and PLGA in DMSO solution. While the weak acid such as acetic acid does not prevent the deleterious interaction/reaction between the peptide and PLGA in DMSO solution.

Example 10

In Vitro Release of Leuprolide from Injectable Polymeric Formulations

Three polymer vehicle solutions were prepared as following: PLG 85/15 (0.28 IV) with a lauryl ester end group was dissolved in NMP at 50% and 55% by weight, and RG503 (0.42 IV) with a carboxylic acid end group was dissolved in NMP at 50% by weight. Then suitable amount of leuprolide hydrochloride (LAHCl) and leuprolide mesylate (LAMS) were mixed with the polymer solutions at 6% by weight each. The formulations were thoroughly mixed to obtain uniform formulations.

Figure 3:
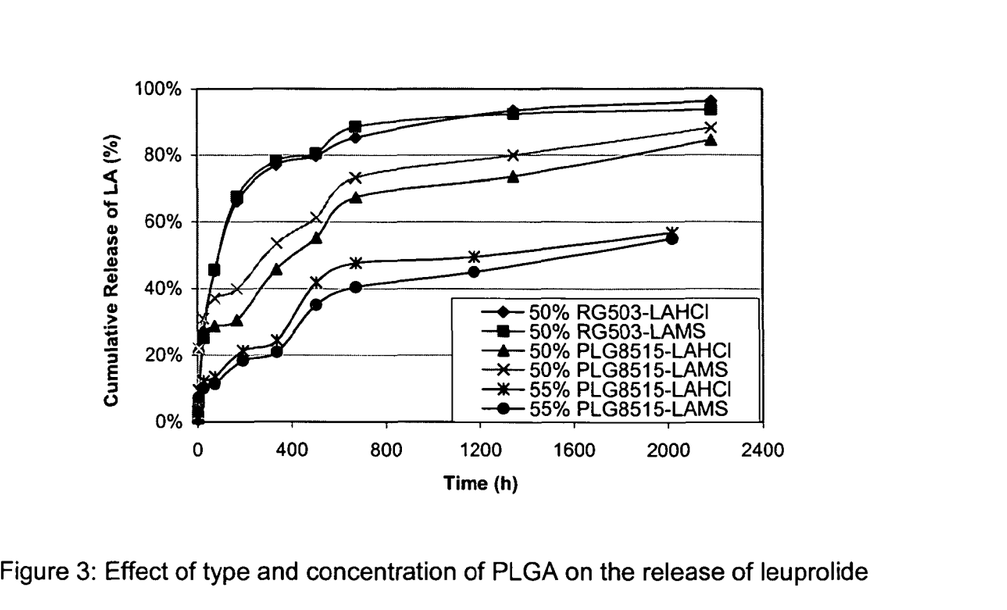
FIG. 3: Effect of type and concentration of PLGA on the release of leuprolide

An aliquot of the formulation suspension (about 100 mg) was injected into in 3 mL phosphate buffer saline solution at pH 7.4 with 0.1% sodium azide at 37° C. The receiving fluid was replaced at selected time points with fresh buffer solution, and the removed buffer solution diluted 2-fold with phosphate buffer at pH 7.4 was analyzed for drug concentration by HPLC. The amount released at each time point was calculated. FIG. 3 shows the cumulative release of leuprolide for different formulations over time.

As shown in FIG. 3, there is no significant difference in leuprolide release between LAHCl and LAMS. However, the type and the concentration of PLGA seem to affect the release of leuprolide significantly. The release rate of leuprolide from RG503H formulation was much faster than that from PLG85/15 formulations. Thus, RG503H may be suitable for shorter-term delivery of leuprolide, while PLG85/15 may be useful for longer-term delivery of the peptide. The release rate of the peptide can also be further modified by changing the concentration of the PLGA. As the concentration of PLG85/15 was increased from 50% to 55%, the initial release rate of leuprolide was significantly reduced. Thus, the parameters for a specific formulation for the peptide to achieve a desired release profile can be readily obtained by simple experimentations.

Example 11

Effect of Excipients on the In Vitro Release of Leuprolide

The polymer vehicle solutions with and without excipients were prepared as following: PLA 100DLPL (0.26 IV, Lakeshore, Ala.) with a lauryl ester end group and Vitamin E TPGS were dissolved in NMP at suitable amount according to the Table 7. Then suitable amount of leuprolide hydrochloride (LAHCl) was mixed with the polymer solutions at 15% by weight. The formulations were thoroughly mixed to obtain uniform formulations.

TABLE 7

Effect of excipients on the in vitro release of leuprolide

| Sample | PLA 100DLPL (%) | NMP (%) | Vitamin E TPGS (%) | LAHCl (%) |
|---|---|---|---|---|
| Formulation-1 | 47 | 38 | 0 | 15 |
| Formulation-2 | 44.5 | 36.4 | 4.2 | 15 |

Figure 4:
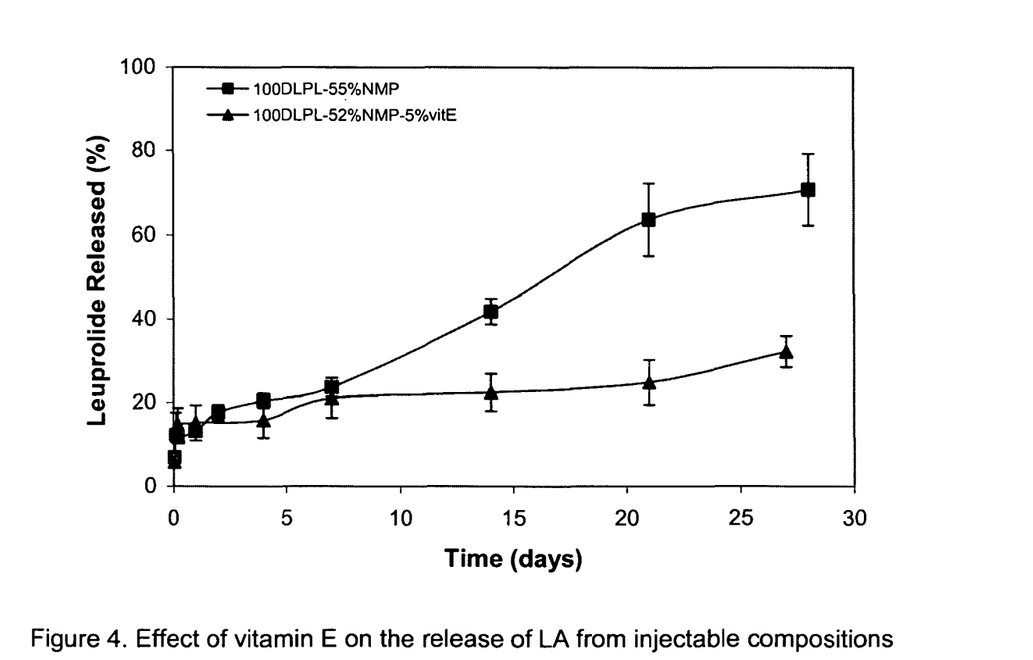
FIG. 4. Effect of vitamin E on the release of LA from injectable compositions

An aliquot of the formulation suspension (about 100 mg) was injected into in 3 mL phosphate buffer saline solution at pH 7.4 with 0.1% sodium azide at 37° C. The receiving fluid was replaced at selected time points with fresh buffer solution, and the removed buffer solution diluted 10-fold with PBS at pH 7.4 was analyzed for drug concentration by HPLC. The amount released at each time point was calculated. FIG. 4 shows the cumulative release of leuprolide for different formulations over time.

As shown in FIG. 4, the incorporation of Vitamin E TPGS did not affect the initial burst, but seemed to reduce the release rate of leuprolide at later stages. Thus, Vitamin E TPGS may be useful for extending the delivery of the peptide and also functioning as an antioxidant.

Example 12

Effect of Excipients on the In Vitro Release of Leuprolide

The polymer vehicle solutions with and without excipients were prepared as following: PLA 100D040 (0.34 IV, Durect, Calif.) with a lauryl ester end group and medium chain triglyceride Miglyol 812 were dissolved in NMP at suitable amount according to the Table 8. Then suitable amount of leuprolide hydrochloride (LAHCl) was mixed with the polymer solutions at 15% by weight. The formulations were thoroughly mixed to obtain uniform formulations.

TABLE 8

Effect of excipients on the in vitro release of leuprolide

| Sample | PLA 100D040 (%) | NMP (%) | Miglyol 812 (%) | LAHCl (%) |
|---|---|---|---|---|
| Formulation-1 | 42.5 | 42.5 | 0 | 15 |
| Formulation-2 | 42.5 | 38.3 | 4.2 | 15 |

An aliquot of the formulation suspension (about 100 mg) was injected into a vial containing 3 mL phosphate buffer saline solution at pH 7.4 with 0.1% sodium azide at 37° C. The receiving fluid was replaced at selected time points with fresh buffer solution, and the removed buffer solution diluted 10-fold with PBS at pH 7.4 was analyzed for drug concentration by HPLC. The amount released at each time point was back calculated using a standard curve. FIG. 5 shows the cumulative release of leuprolide for different formulations over time.

As shown in FIG. 5, the incorporation of Miglyol 812 did significantly reduced the initial burst release of leuprolide, and seem to maintain the release rate of leuprolide at later stages. Thus, Miglyol 812 may be useful for extending the delivery of the peptide. Comparing to the results in Example 11, it seems the molecular weight of the polymer also significantly affect the initial burst release of leuprolide. It seems that the smaller molecular weight of the PLA, the smaller the initial burst release rate of leuprolide.

Example 13

In Vivo Release of Leuprolide

Poly(DL-lactide-co-glycolide) of an 85/15 ratio of lactide to glycolide (DLPLG85/15, IV: 0.28) containing a lauryl ester end group was dissolved in N-methyl-2-pyrrolidone (NMP) to give a 55% solution by weight. The leuprolide salt, i.e., Leuprolide mesylate or Leuprolide HCl, were mixed with the PLGA solution in NMP to give a uniform injectable formulation at a drug loading of about 12%. The injectable formulations were transferred into 1.2 ml polypropylene syringes with luer-lock tips and a 19 gauge thin-wall needle attached. Each formulation was then injected into the rats subcutaneously at a volume of about 100 µL with 6 animals per group. The serum samples were collected from each animal at 3 hour, 1, 3, 7, 14, 28, 42, 56, and 70 days post injection. The serum samples were analyzed for leuprolide concentration by ELISA using the kits available from Peninsula Laboratories Inc. The leuprolide remaining in the implants at various times was analyzed by HPLC.

Figure 6:
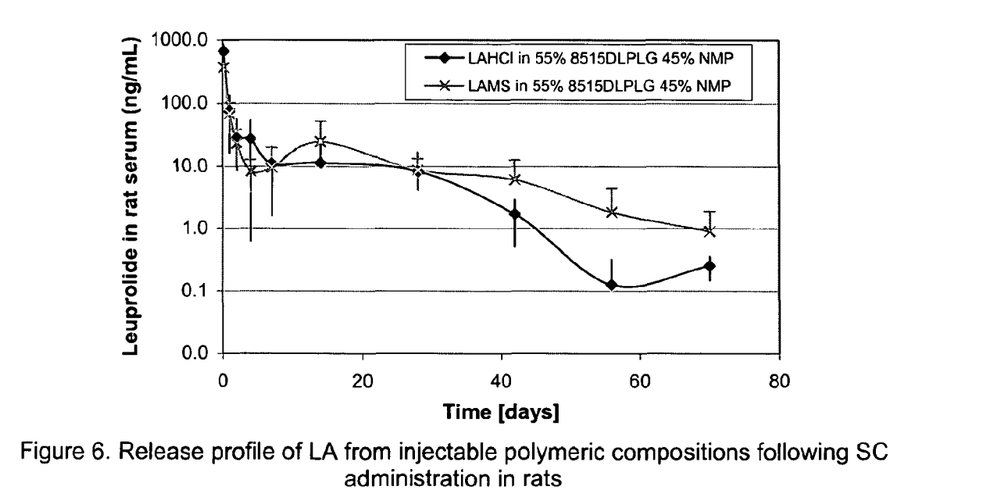
FIG. 6. Release profile of LA from injectable polymeric compositions following SC administration in rats

FIG. 6 shows the release profile of leuprolide from two different formulations up to 70 days. Both formulations showed initial burst release of leuprolide. The formulation containing LAHCl reached $C_{max}$ of 661.6 ng/mL at 3 hours, and the formulation containing LAMS reached $C_{max}$ of 370.6 ng/mL also at 3 hours. Both formulations showed sustained release of leuprolide over an extended time period. The formulation containing LAMS showed a more constant serum levels of leuprolide than that obtained from the formulation containing LAHCl.

Example 14

In Vivo Release of Leuprolide

Poly(DL-lactide-co-glycolide) of a 85/15 ratio of lactide to glycolide (DLPLG85/15, IV: 0.27) containing a 1,6-hexanediol moiety is dissolved in N-methyl-2-pyrrolidone (NMP) to give a 50% solution by weight. The leuprolide salt, i.e., Leuprolide acetate or Leuprolide HCl, are mixed with the PLGA solution in NMP to give a uniform injectable formulation at a drug loading of about 12%. The injectable formulations are transferred into 1.2 ml polypropylene syringes with luer-lock tips and a 19 gauge thin-wall needle attached. Each formulation is then injected into the rats subcutaneously at a volume of about 100 µL with 6 animals per group. The serum samples are collected from each animal at 3 hour, 1, 3, 7, 14, 28, 42, 56, 70, 91, 112, 133, 154, 175, and 206 days post injection. The serum samples are analyzed for leuprolide concentration by ELISA using the kits available from Peninsula Laboratories Inc., and for testosterone concentration by LC/MS/MS. The leuprolide remaining in the implants at various times may be analyzed by HPLC.

Similar experiments can be designed and performed using other LHRH analogues such as buserelin, deslorelin, fertirelin, histrelin, lutrelin, goserelin, nafarelin, triptorelin, cetrorelix, abarelix, and other peptides, such as GLP-1, PYY, etc, and other polymers and solvents.

Example 15

Use of the Stabilized Injectable Polymeric Compositions

The administration of the stabilized injectable polymeric composition to a patient may be accomplished in a number of ways. A biodegradable polymeric composition may be injected subcutaneously or intramuscularly to form an implant in situ, applied as a transdermal cream, and also introduced to the patient as a rectal or vaginal suppository.

Example 16

Preparation of Polymer Microspheres Containing LAHCl

Poly(lactide-co-glycolide) (PLGA) microspheres are prepared by an oil-in-water (O/W) single emulsion technique. PLGA is dissolved in methylene chloride (DCM). For the encapsulation of LAHCl, the drug is mixed with the PLGA solution in DCM. The mixed solution or suspension is emulsified in 500 mL of 0.5-1% (w/v) PVA (PVA, 88% hydrolyzed, average molecular weight of 31,000-50,000, Sigma-Aldrich) solution pre-cooled in the refrigerator at 4° C. The emulsion is stirred continuously for 3 h at RT to evaporate the DCM. The hardened microspheres are collected, washed three times with deionized water, and then freeze-dried.

Example 17

Use of the Stabilized Liquid Polymeric Composition for Preparing Implantable Polymer Matrices The biodegradable polymer consisting of a poly-(lactic acid-co-glycolic acid) having a ratio of lactide to glycolide of 50:50 to 100:0 such as RG503H (Boehringer Ingelheim Chemicals, Inc. USA) is dissolved in a volatile organic solvent, such as ethyl acetate or methylene chloride. An appropriate amount of a beneficial salt as defined herein such as goserelin mesylate (0.01%-30% by weight relative to the polymer) is dissolved/dispersed in the polymer solution. The solution is thoroughly mixed to obtain a uniform solution or suspension. After the mixing is complete, the solvent is removed by evaporation. This is done by a spray drying procedure to form small uniform particles for injection. This can be done also in a mold to form an implant. The resulting polymer matrices can also be ground to a powder and formulated as an injectable suspension.

Thus obtained solid dosage forms can be injected subcutaneously or intramuscularly, or can be placed surgically under the skin in the form of an implant, or given orally as part of an oral delivery system for peptide agents. The solid microparticles may also be prepared as a suspension or a non-aqueous solution, which may also be administered to a patient via inhalation, for pulmonary drug delivery. The microparticles may also be suspended in oil and introduced to the patient as a rectal or vaginal suppository.

What is claimed is:

1. An injectable polymeric composition comprising:
    a) a mesylate salt of leuprolide;
    b) a biodegradable polymer selected from the group of polylactide, poly(lactic acid), poly(lactic acid-co-glycolic acid), and poly(lactide-co-glycolide); and
    c) N-methyl-2-pyrrolidone (NMP),
    wherein the composition does not contain excess strong acid in addition to the strong acid used to form the mesylate salt of leuprolide.

2. The injectable polymeric composition of claim 1, wherein the biodegradable polymer has a weight average molecular weight of between about 2,000 to about 100,000 dalton.

3. The injectable polymeric composition of claim 1 comprising:
    a) 0.01-40% w/w leuprolide mesylate;
    b) 40-60% w/w the biodegradable polymer selected from the group consisting of polylactide and poly(lactic acid); and
    c) 30-80% w/w N-methyl-2-pyrrolidone,
    wherein the composition does not contain excess strong acid in addition to the strong acid used to form the leuprolide mesylate.

4. The injectable polymeric composition of claim 3, wherein the biodegradable polymer has an average molecular weight of about 8,000 to about 50,000.

5. An injectable polymeric composition of claim 1 comprising:
    a) 0.01-40% w/w leuprolide mesylate;
    b) 30-60% w/w biodegradable polymer selected from the group consisting of poly(lactide-co-glycolide) and poly(lactic acid-co-glycolic acid), having the ratio of lactide:glycolide or lactic acid:glycolic acid of from 50:50 to about 100:0; and
    c) 30-80% w/w N-methyl-2-pyrrolidone,
    wherein the composition does not contain excess strong acid in addition to the strong acid used to form the leuprolide mesylate.

6. The injectable polymeric composition of claim 5, wherein the poly(lactide-co-glycolide) or poly(lactic acid-co-glycolic acid) has a ratio of lactide:glycolide or lactic acid:glycolic acid of about 85:15.

7. The injectable polymeric composition of claim 5, wherein the poly(lactide-co-glycolide) or poly(lactic acid-co-glycolic acid) has an average molecular weight of about 15,000 to about 50,000.

* * * * *